United States Patent [19]

Plueddemann

[11] Patent Number: 5,006,573

[45] Date of Patent: Apr. 9, 1991

[54] SILANE COUPLING AGENTS

[75] Inventor: Edwin P. Plueddemann, Midland, Mich.

[73] Assignee: Dow Corning Corporation, Midland, Mich.

[21] Appl. No.: 917,950

[22] Filed: Oct. 14, 1986

Related U.S. Application Data

[62] Division of Ser. No. 803,043, Nov. 29, 1985, Pat. No. 4,650,889.

[51] Int. Cl.$^5$ ................................................. C08K 9/08
[52] U.S. Cl. .................................... 523/214; 523/213; 427/387; 427/407.2; 427/409; 528/25; 528/26
[58] Field of Search ................. 523/213, 214; 427/387, 427/407.2, 409; 528/25, 26

[56] References Cited

U.S. PATENT DOCUMENTS

| | | | |
|---|---|---|---|
| 2,718,516 | 9/1955 | Bortnick | 260/86.1 |
| 2,821,544 | 1/1958 | Holtschmidt | 260/486 |
| 3,258,477 | 6/1966 | Plueddemann et al. | 260/448.8 |
| 3,671,562 | 6/1972 | Pepe et al. | 260/488.8 R |
| 4,278,809 | 7/1981 | Burdett | 560/222 |

*Primary Examiner*—John C. Bleutge
*Assistant Examiner*—Ralph H. Dean, Jr.
*Attorney, Agent, or Firm*—Alexander Weitz

[57] ABSTRACT

A novel organosilane coupling agent is disclosed and its use as an adhesion promoter in mineral-filled unsaturated polymer systems is described. Additionally, use of the organosilane as a primer for various substrates is presented. The coupling agent comprises the reaction product of an isocyanatoalkyl ester of acrylic or methacrylic acid with an aminoorganosilane. The organosilane so formed links the acryloxyalkyl or methacryloxyalkyl functionality to an alkylene, or aminoalkylene, group on the silicon atom through a urea group. Use of the organosilane as a coupling agent in a mineral-filled unsaturated polymer results in superior resistance to moisture, particularly when the polymer is selected from the group of corrosion resistant unsaturated polyesters.

19 Claims, No Drawings

SILANE COUPLING AGENTS

This is a divisional of co-pending application Ser. No. 06/803,043 filed on Nov. 29, 1985, now U.S. Pat. No. 4,650,889.

This invention relates to the field of silane coupling agents. More specifically, this invention relates to a silane coupling agent wherein an acrylic radical is connected to a silicon atom through a urea linkage, and said silicon atom is, in turn, connected to at least two hydrolyzable groups. It further relates to a process of using said silane to augment the water-resistance of mineral-filled unsaturated resins.

BACKGROUND OF THE INVENTION

Silane coupling agents have been known to improve the mechanical properties of filled thermosetting and thermoplastic resins since the late 1940's. These low molecular weight compounds are believed to form chemical links between filler particles and polymer molecules, and as such, they must incorporate functional groups capable of reacting with filler and resin alike. Thus, for example, in the modification of unsaturated polymers, or polymerizable monomers, the silane coupling agent typically also contains an unsaturated radical, such as methacrylate, which can graft onto the polymer through a free-radical reaction (e.g., during cure of the resin). The other reactive groups of the silane coupling agent are typically species such as alkoxy or halide groups on silicon, which, when hydrolyzed, can enter into reaction with surface hydroxyl groups of the filler to form a chemical (probably ionic) bond.

Such a silane coupling agent was disclosed by Plueddemann in U.S. Pat. No. 3,258,477, hereby incorporated by reference, and has survived as an industry standard for fiberglass-filled unsaturated polyesters for many years. Plueddemann teaches the use of a silane having the general formula

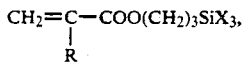

wherein R is H or the methyl radical and X represents the hydrolyzable group referred to above. This silane coupling agent was shown to improve retention of flexural strength of laminates of glass cloth impregnated with an unsaturated polyester resin after exposure to boiling water for two hours. This result was significant in that it is precisely the rapid deterioration of strength, and often electrical properties, after exposure to water that severely limits the utility of polyester composites when coupling agents are not employed.

A similar improvement in resistance to moisture, albeit under relatively mild conditions (water at 50° C./16 hours) was disclosed by Pepe et al. in U.S. Pat. No. 3,671,562 for a composite of glass beads in phenol-formaldehyde resin. Pepe et al. teach a silane coupling agent having a terminal urea radical which is connected to silicon through an organic group. The silicon, in turn, is attached to at least one hydrolyzable group and may also be attached to another silicon through an oxygen linkage to form a siloxane therewith. Remaining free valences on the first silicon atom are bonded to organic groups which may include alkenoyloxyalkyl.

One of the major drawbacks of composites based on traditional polyesters has been the relatively poor resistance to moisture of the base resin. This, in turn, is due to the relative ease of hydrolysis of the ester linkage. In this regard, development of so-called "corrosion resistant" polyesters, such as the isophthalates, teraphthalates and acrylicmodified epoxies, has been a significant advance. These resins offer considerably improved retention of mechanical properties after exposure to moisture, or aqueous acids and bases. For composites based on corrosion resistant resins, exposure to boiling water for two hours is no longer considered an adequate criterion of performance, since the resin itself is capable of much greater resistance to hydrolysis. In order to distinguish performance enhancement imparted by a given coupling agent, a 24-hour residence in boiling water is considered more representative. This is based on the observation that exposure (e.g., 72 hour boiling water) generally does not lead to further strength reduction of a composite containing no coupling agent (i.e., corrosion resistant polyester control).

It has now been found that a silane coupling agent, comprising the reaction product of an isocyanatoalkyl ester with an aminoorganosilane, can impart superior moisture resistance to mineral-filled unsaturated polyesters, as well as other unsaturated resin composites.

SUMMARY OF THE INVENTION

This invention relates to an organosilane of the formula

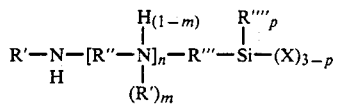

wherein R' is the group

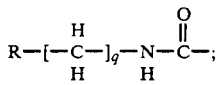

R is selected from the group consisting of acryloxy and methacryloxy radical; R" is a divalent hydrocarbon radical having 2 to 4 carbon atoms; R''' is a divalent hydrocarbon radical having 3 to 6 carbon atoms; R'''' is selected from the group consisting of methyl, ethyl, propyl, butyl, and phenyl; X is a hydrolyzable species selected from the group consisting of methoxy, ethoxy, acetoxy and chlorine; n is 0, 1 or 2; q is 2, 3 or 4; p is 0 or 1; and m has an average value from 0 to 1.0 when n is at least 1.

This invention also relates to a process for bonding a polymerizable material to a mineral filler comprising: (a) mixing the above described organosilane with a polymerizable material having aliphatic unsaturation and a filler having hydroxyl functionality thereon, to obtain a uniform dispersion of the components; and (b) polymerizing said material to form a solid composite.

This invention further relates to a method for priming a surface having hydroxyl functionality thereon to improve its bonding to organic resins containing aliphatic unsaturation in the uncured state, comprising wetting said surface with the above described organosilane and then drying said surface.

This invention still further relates to an article of manufacture, comprising, in a dispersed and chemically reacted combination, a mineral filler; a polymerized resin, which prior to polymerization contained aliphatic unsaturation; and the organosilane described above.

DETAILED DESCRIPTION OF THE INVENTION

The silane coupling agents of this invention may be used to enhance the mechanical properties of mineral-filled unsaturated resin composites, particularly after prolonged exposure to boiling water. The resins which derive the greatest benefit from use of these coupling agents are the corrosion resistant unsaturated polyesters, such as the isophthalates, teraphthalates and acrylic-modified epoxies. These resins are well known in the art. Other resins which may be employed in combination with the silanes of the instant invention include bis-maleimides, poly(1,2 butadiene) and acetylenic-terminated polyimides, all well known in the art.

Additionally, the silanes of this invention may be incorporated into formulations comprising polymerizable monomers, or monomer mixtures, having aliphatic unsaturation, and mineral fillers. In such systems, monomers are caused to polymerize in the presence of filler and coupling agent to form a solid composite. Examples of such monomers are styrene, methyl acrylate, methyl methacrylate and poly-functional acrylic monomers known in the art.

A plurality of mineral fillers, which are typically used to reinforce the above resins, may be employed in the instant invention. In the current context, "mineral filler" refers to inorganic material which may be of natural or synthetic origin. All these fillers have a common feature, however, in that their surfaces contain hydroxyl functionality to a greater or lesser extent. The hydroxyl groups can react with the silanol groups formed upon hydrolysis of the hydrolyzable groups X of the silane coupling agent. Notable within this general category of fillers are the siliceous materials such as glass fiber, precipitated silica, ground quartz, aluminum silicate, zirconium silicate, calcium silicate, glass micro beads, mica, asbestos, clay, vitreous enamels and ceramics. Other examples of suitable fillers include alumina, silicon carbide, and silicon whiskers. In addition to the filler, other components, such as catalysts, pigments, stabilizers and antioxidants may be included in the filled resin formulation.

Methods of incorporating silane coupling agents to improve performance of filled resins are well known in the art. For example, the silane coupling agents of this invention may be added directly to a blend of catalyzed resin (or polymerizable monomer mix) and filler. The resulting mixture is subjected to intensive mixing to fully disperse the filler. The silane coupling agents of this invention may be added neat or as a dispersion in water, or as a solution in a solvent, such as isopropanol. Methods of dispersing silane coupling agents in water are known in the art and are described in detail by Plueddemann, cited supra. Alternatively, the filler may first be treated with the corresponding amount of silane by a dry blending method, such as tumbling in a container, or by mechanical mixing, followed by drying in air at about 100° C. This treated filler may then be dispersed in catalyzed resin (or polymerizable monomer mix), as described above. After mixing with resin, the mixture is generally de-gased under vacuum, which procedure also removes the bulk of any solvent which may have been utilized. Finally, the mixture may be molded and cured (polymerized in situ when monomers are used) according to well established methods in the art. The latter method, wherein the filler is pretreated, generally leads to better mechanical performance.

The resulting molded article, wherein the disclosed organosilanes are used as coupling agent, is within the scope of this invention.

Any means capable of inducing polymerization of vinylic unsaturation may be employed to accelerate the cure of resin or to polymerize the monomer. Although means such as heat, ultra-violet radiation and catalysts find utility, it is the last of these which is most widely used. The catalysts employed are typically the organic peroxides, (e.g., benzoyl peroxide) and azo compounds (e.g., azobisisobutyronitrile). Benzoyl peroxide is a common catalyst for the unsaturated polyesters and is generally added at about 0.2 to 1.0 parts by weight, based on the resin.

The silanes of this invention, on a solvent-free basis, may be added at a concentration of 0.1 to 1.0% of the total weight of resin plus filler, 0.25% being preferred.

In accordance with another aspect of the present invention, the silane coupling agents may be used to prime various substrates such as glass, metals having an oxide surface thereon, mica, asbestos, clay, vitreous enamel, silicon, silicon carbide, alumina and ceramics, inter alia. Methods for using silane coupling agents as primers are well known in the art. Typically, the surface of a substrate is wetted by the coupling agent by dipping, brushing, spraying, or wiping, for example. As before, the silane may be applied from solution or dispersion, the preferred method being application from aqueous solution or dispersion at about a 10% (by weight) concentration. After application, the primed surface is usually dried to remove any solvent or water employed. The primed surfaces of this invention form water-resistant bonds with the unsaturated resins cited above when said resins are cured thereupon. Such primed substrates, wherein the disclosed silanes are employed as primers, are also within the scope of the present invention.

The silane coupling agents of this invention may be prepared by reacting an isocyanatoalkyl ester of the general formula

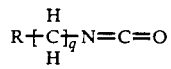

with an aminoorganosilane of the general formula

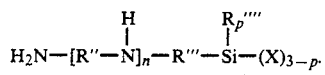

In the formula for said isocyanatoalkyl ester, R represents either acryloxy or methacryloxy group and q is an integer between two and four, inclusive. The preferred isocyanatoalkyl ester is 2-isocyanatoethyl methacrylate (IEM). In the formula for said aminoorganosilane, R" represents a hydrocarbon radical having 2 to 4 carbon atoms such as ethylene, trimethylene or tetramethylene. The divalent hydrocarbon radical R''' may contain from 3 to 6 carbon atoms, including such groups as trimethylene, tetramethylene, methyltrimethylene, pentamethylene and hexamethylene. The organic group R'''' may be selected from the group consisting of methyl, ethyl, propyl, butyl and phenyl. The hydrolyzable species X may be selected from the group methoxy, ethoxy, acetoxy and chlorine. Finally, n is an integer between zero and two, inclusive, and p is zero or one. Preferred aminoorganosilanes are N-gamma-aminopropyltriethoxysilane and N-beta-aminoethyl-gamma-aminoproyltrimethoxysilane, the latter being most preferred.

The molar ratio of isocyanatoalkyl ester to said aminoorganosilane may be varied from 1.0 to (1 +n) within the scope of this invention to yield a organofunctional silane having the general formula

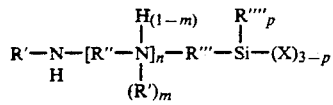

wherein R' is the group

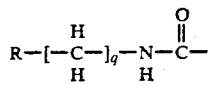

and the various symbols have been previously defined. When the aminoorganosilane contains more than one amine group (i.e., when n is at least one), the average value of m may range from zero to one, according to the molar ratio of reactants employed.

Reaction between the isocyanatoalkyl ester and the aminoorganosilane is facile and usually complete within ten minutes at 25° C., so that heating is not necessary. Formation of urea linkage has been confirmed by infrared analysis, as well as indirectly by an observed exotherm during reaction. Furthermore, the reactants can be mixed neat or in solvents such as dimethoxyethane, toluene, dioxane and tetrahydofuran. Additionally, secondary or tertiary alcohols may be used as solvents since these react very slowly with the isocyanate group of the isocyanatoalkyl ester relative to reaction of isocyanate with the amine of the aminoorganosilane. It is thus convenient to prepare the silane of this invention in a 50% (by weight) solution of isopropyl alcohol and utilize it in this form. After reaction is complete, the mixture is cooled and a small quantity of alcohol, such as methanol, is generally added to react with any remaining isocyanate functionality.

If the preferred aminoorganosilane, N-beta-aminoethyl-gamma-aminopropyltrimethoxyisilane, and the preferred isocyanatoalkyl ester, 2-isocyanatoethyl methacrylate (IEM) are employed, the silanes of this invention are water dispersible or soluble when the molar ratio of IEM to N-beta-aminoethyl-gamma-aminopropyltrimethoxysilane is in the range of 1.0 to 1.75. Methods which may be used to disperse silane coupling agents in water are described by Plueddemann, cited supra. The water dispersions of the silanes of this invention represent a commercially desirable embodiment and a value of about 1.5 for the molar ratio of IEM to N-beta-aminoethyl-gamma-aminopropyltrimethoxyisilane is most preferred.

Examples of suitable aminoorganosilanes include compounds represented by the following formulas.

$$H_2N-CH_2CH_2NH-CH_2CH_2CH_2Si(OCH_3)_3 \quad (I)$$
$$H_2N-CH_2CH_2CH_2Si(OCH_2CH_3)_3 \quad (II)$$
$$H_2N-(CH_2CH_2NH)_2-CH_2CH_2CH_2Si(OCH_3)_3 \quad (III)$$

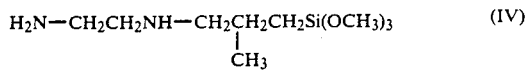

The aminoorganosilanes are well known in the art and are typically formed by reacting chloroalkylalkoxysilanes with organic amines. The resulting aminoorganosilanes are generally not pure species and several side products coexist with the main components. The aminoorganosilane of formula I, above, is available commercially as Dow Corning ® Z-6020 (Dow Corning Corp., Midland, MI). For the purposes of this invention, either the crude reaction products or purified components may be employed, distilled N-beta-aminoethyl-gamma-aminopropyltrimethoxyisilane (formula I, above) being preferred.

The isocyanatoalkyl esters are known in the art and may be prepared by methods described in U.S. Pat. Nos. 2,718,516 and 2,821,544, the full disclosures of which are hereby incorporated by reference. The preferred 2-isocyanatoethyl methacrylate (IEM) reactant is a commercial product of the Dow Chemical Company, Midland, MI, available under the designation XAS 10743.00. A typical preparation of IEM comprises reacting an aqueous solution of 2-isopropenyl2-oxazoline with an organic solution of phosgene in the presence of an acid acceptor. This process has been described in detail in U.S. Pat. No. 4,278,809, which is hereby also incorporated by reference.

The following examples are offered for the purpose of illustration and should not be construed as limiting the claimed invention. Unless noted to the contrary, proportions are on a weight basis.

EXAMPLE 1

Into a 3-neck flask equipped with a stirrer, a thermometer and a vented addition funnel, were added 22 g (0.1 mole) of distilled N-beta-aminoethyl-gamma-aminopropyltrimethoxysilane and 53 g of dimethoxyethane solvent. While stirring this solution, 31 g (0.2 mole) of 2-isocyanatoethyl methacrylate (IEM), Experimental Monomer XAS 10743.00, (Dow Chemical Co., Midland, MI) was added. As a result of the exothermic reaction, the temperature climbed to about 70° C. After cooling the product, 5 g of methanol was added in order to react with any remaining isocyanate functionality. The molar ratio of IEM to N-beta-aminoethyl-gamma-aminopropyltrimethoxysilane in this example is 2.0.

EXAMPLE 2

The procedure of Example 1 was followed to produce urea-functional silanes having an average molar ratio of 1.0, 1.25, 1.5, and 1.75 of IEM to N-beta-aminoethyl-gamma-aminopropyltrimethoxysilane.

EXAMPLE 3

The method of Example 1 was employed to react 22 g (0.1 mole) of N-gamma-aminopropyltriethoxysilane with 15.5 g (0.1 mole) of IEM. No solvent was included during the reaction. After cooling, 37.5 g of methanol was added to give a 50% solution of the product.

EXAMPLE 4

Organofunctional silanes, prepared according to Examples 1 and 3, as well as a comparison silane, were evaluated in 20 wollastonite-filled polyester resin.

Nyad® 400, (Nyco Division of Processed Mineral, Inc., Willsboro, NY) is described as an acicular particulate calcium silicate with an average particle size of eight microns. Fifty parts of Nyad® 400 were mixed with 50 parts of CoRezyn® 5500 (Interplastics Corp., Minneapolis, Minn.), 0.25 parts benzoyl peroxide catalyst and 0.25 parts (solids basis) of the various silanes of this example. CoRezyn® 5500 is described as a rigid isophthalate polyester diluted in styrene monomer. Mixing was accomplished by first blending in an eight-ounce jar with a spatula, then mixing till smooth in a high shear mixer. The latter step resulted in a temperature rise to about 75° C. The mixtures were de-aired for about one minute under a reduced pressure of approximately 10 to 20 mm mercury and cast into 10 x 150 mm Pyrex® test tubes which were previously coated with a silicone release agent. During the de-airing step, the bulk of any solvent present was driven off. After curing overnight in a 100° C. air oven, the cast rods were removed by tapping the test tubes. The rods were tested for flexural strength by a 3-point loading method according to American Society for Testing and Materials (ASTM) method D790-81, using a 1.75 inch span. Duplicate rods were exposed to boiling water for 24 hours and similarly tested for flexural strength. Results are presented in Table I. In this, and subsequent tables, the column entitled "% Improvement Over Control" refers to flexural strength measurements of the sample and control castings after exposure to boiling water for 24 hours. For example, for the gamma-MPS (gamma-methacryloxypropyltrimethoxysilane) sample, the % Improvement is calculated according to:

$$100 \times (117-92)/92 = 28\%.$$

TABLE 1

| WOLLASTONITE-FILLED POLYESTER CASTINGS | | | |
|---|---|---|---|
| Adhesion Promoter Added to Casting Mix (0.25%) | Flexural Strength (MPa at 1.75" span) | | % Improvement Over Control |
| | Dry | After 24 hrs. in Boiling Water | |
| None (Control) | 132 | 92 | — |
| IEM (No silane) (For Comparison) | 134 | 93 | 1 |
| γ-MPS (For Comparison) | 148 | 117 | 27 |
| Reaction Product of 1 mole IEM with | 149 | 112 | 22 |
| 1 mole (II) Reaction Product of 2 moles IEM with 1 mole (I) | 186 | 162 | 76 |

IEM = 2-isocyanatoethyl methacrylate
(II) = N-gamma-aminopropyltriethoxysilane
(I) = N-beta-aminoethyl-gamma-aminopropyltrimethoxysilane
γ-MPS = gamma-methacryloxypropyltrimethoxysilane

EXAMPLE 5

Rods were prepared and tested according to the methods described in Example 4 using a novacite filler. Daper® (Malvern Minerals, Hot Springs, Ark.), is described as a natural noviculite silica having an average particle size of 5.5 microns. Fifty parts of Daper were mixed with 50 parts of catalyzed CoRezyn® 5500 (0.25 parts benzoyl peroxide) and 0.25 parts of the various coupling agents. The span used in flexural testing was 2.00 inches in this case. Additionally, water dispersions of the various silanes were prepared according to methods described by Plueddemann, cited supra, and the dispersions characterized visually. Results are presented in Table II.

TABLE II

| 50% (By Weight) Novacite-Filled CoRezyn® 5500 Castings | | | | |
|---|---|---|---|---|
| Coupling Agent (0.25%) | Dispersion of Coupling Agent in Water | Flexural Strength (MPa) | | % Improvement Over Control |
| | | Dry | After 24 hrs. in Boiling Water | |
| None (Control) | — | 100 | 68 | — |
| γ-MPS (For Comparison) | Clear | 110 | 101 | 48 |
| Reaction Product of 1.0 mole of (I) with: | | | | |
| 1.0 mole IEM | Clear | 141 | 124 | 82 |
| 1.25 moles IEM | Very Slight Haze | 141 | 128 | 89 |
| 1.50 moles IEM | Slight Haze | 145 | 130 | 91 |
| 1.75 moles IEM | Hazy | 140 | 134 | 97 |
| 2.00 moles IEM | Cloudy | 141 | 138 | 103 |
| Reaction Product of 1.0 mole of (II) with 1.0 mole of IEM | Cloudy | 121 | 121 | 78 |

γ-MPS = gamma-methacryloxypropyltrimethoxysilane
IEM = 2-isocyanatoethyl methacrylate
(I) = N-beta-aminoethyl-gamma-aminopropyltrimethoxysilane
(II) = N-gamma-aminopropyltriethoxysilane

EXAMPLE 6

Glass microbeads having the composition of E-glass and an average diameter of 30 microns (3000-E from Potters Industries, Hasbrouck, NJ) were treated with various coupling agents at a level of 0.25% (solids basis). A dry blending technique, which comprised tumbling the filler and silane in a jar for approximately one hour at about 25° C, was employed. Mixtures containing 60 parts of these treated fillers and 40 parts of a catalyzed (0.5% benzoyl peroxide based on resin), styrenediluted, isophthalic polyester, Stypol 40-2988 (Freeman Chemical Co., Port Washington, WI), were prepared by the methods described in Example 4. Cured rods of these compositions were tested for flexural strength using a 2.00 inch span. Results are shown in Table III. In the comparative 5 examples of this table, the coupling agent Volan® (E. I. Du Pont de Nemours and Co., Wilmington, Del.), is described as a complex in which a trivalent chromium atom is coordinated with methacrylic acid.

TABLE III

60/40 GLASS MICROBEADS (P-3000-E) FILLED POLYESTER (STYPOL 40-2988) (0.25 Percent Pretreatment on Beads)

| Pretreatment on Glass | Flexural Strength of Castings (MPa) | | % Improvement Over Control |
|---|---|---|---|
| | Dry | After 24 hrs. in Boiling Water | |
| None (Control) | 82 | 41 | — |
| Vinyltrimethoxysilane (For Comparison) | 92 | 64 | 57 |
| Volan ® (0.5%) (For Comparison) | 108 | 68 | 65 |
| γ-MPS (For Comparison) | 112 | 94 | 129 |
| Reaction Product of 1.0 mole of (I) with 2.0 moles of IEM | 141 | 112 | 173 |

γ-MPS = gamma-methacryloxypropyltrimethoxysilane
(I) = N-beta-aminoethyl-gamma-aminopropyltrimethoxysilane
IEM = 2-isocyanatoethyl methacrylate

EXAMPLE 7

Rods were prepared and tested according to the methods described in Example 4 using a silica-filled polyester. Fifty parts of 5 micron Min-U-Sil ®, a high purity crystalline silica (Pennsylvania Glass Sand, Pittsburgh, Pa.) were mixed with 50 parts catalyzed (0.5% benzoyl peroxide based on resin) CoRezyn ® 5500 and 0.25 parts of the silane of Example 1, as well as comparative silanes. Flexural strength results using a test span of 1.75 inches, are shown in Table IV.

TABLE IV

Silica-Filled Polyester Castings (5 Micron Min-U-Sil/CoRezyn ® 5500)

| Coupling Agent | Flexural Strength (MPa) | | % Improvement Over Control |
|---|---|---|---|
| | Dry | After 24 hrs. in Boiling Water | |
| None (Control) | 130 | 112 | — |
| γ-MPS (For Comparison) | 215 | 147 | 31 |
| Z-6032 (For Comparison) | 223 | 182 | 62 |
| Reaction Product of 1.0 mole (I) with 2.0 moles of IEM | 236 | 212 | 90 |

γ-MPS = gamma-methacryloxypropyltrimethoxysilane
Z-6032 = Dow Corning ® Z-6032, Vinyl benzyl cationic silane
(I) = N-beta-aminoethyl-gamma-aminopropyltrimethoxysilane
IEM = 2-isocyanatoethyl methacrylate

EXAMPLE 8

Various silanes of this invention were compared with standard silane coupling agents with respect to performance as primers for glass (i.e., a simulation of adhesion to glass fibers in a fiberglass composite). The silanes were applied to precleaned glass microscope slides by wiping with a paper tissue saturated with 10% (by weight) solutions of the silanes in isopropyl alcohol. After drying the primed slides for about 15 minutes at room temperature, a thin film of catalyzed 0 polyester resin, CoRezyn ® 5500, was applied and cured on the slide for 30 minutes at 130° C. The adhesion of these polyester films was rated before and after submersion in boiling water for two hours. This procedure comprised prying or scraping the films from the glass slides using a razor blade. Results are presented in Table V, wherein the following rating scheme pertains:

| Rating | Observation |
|---|---|
| 0 | Floated free of glass slide (adhesive failure). |
| 1 | Could be removed in one piece with razor blade (adhesive failure). |
| 2 | Could be pried off in pieces (adhesive and cohesive failure). |
| 3 | Came off with difficulty; some glass also peeled off (cohesive failure). |
| 4 | Could not be removed from glass (cohesive failure). |

TABLE V

CURED POLYESTER (CoRezyn ® 5500) FILMS ON GLASS

| Primer Composition | Adhesion of Film to Glass | |
|---|---|---|
| | Dry | After 2 hrs. in Boiling Water |
| None (Control) | 3 | 0 |
| γ-MPS (For Comparison) | 4 | 3 |
| Z-6032 (Cationic styryl silane) (For Comparison) | 4 | 2 |
| Reaction Product of 1.0 mole (II) with 1.0 mole IEM | 4 | 1 |
| Reaction Product of 1.0 mole (I) with 1.0 mole IEM | 4 | 2 |
| Reaction Product of 1.0 mole (I) with 2.0 moles IEM | 4 | 4 |
| Reaction Product of 1.0 mole (III) with 3.0 moles IEM | 4 | 4 |

γ-MPS = gamma-methacryloxypropyltrimethoxysilane
Z-6032 = Dow Corning ® Z-6032, Vinyl benzyl cationic silane
(I) = N-beta-aminoethyl-gamma-aminopropyltrimethoxysilane
(II) = N-gamma-aminopropyltriethoxysilane
(III) = $H_2NCH_2CH_{2H}NCH_2CH_{2H}N(CH_2)_3Si(OCH_3)_3$
IEM = 2-isocyanatoethyl methacrylate

EXAMPLE 9

A method similar to that of Example 1 was employed to prepare an organosilane of the present invention wherein three moles of 2-isocyanatoethyl methacrylate were reacted with one mole of the aminoorganosilane having the formula

$$H_2N-(CH_2CH_2NH)_2-CH_2CH_2CH_2Si(OCH_3)_3$$

Precleaned glass microscope slides and aluminum panels were primed with a 10% isopropanol solution of the above silane, as well as comparative silanes, according to methods of Example 8. Adhesion, before and after boiling water immersion, was evaluated. Results are presented in Table VI.

In all cases, the organosilane coupling agents of this invention proved superior to, or at least as good as, comparison coupling agents with respect to flexural strength after immersion in boiling water for 24 hours. The organosilanes of this invention were also superior to (or as good as) the comparative silanes when each was used to prime glass or aluminum substrates.

TABLE VI

Adhesion of Cured Polyester on Primed Surfaces

| Primer | Substrate | | | |
|---|---|---|---|---|
| | Glass | | Aluminum | |
| | Dry | After 4 hrs. in Boiling Water | Dry | After 4 hrs. in Boiling Water |
| γ-MPS (For Comparison) | Excellent | Good | Excellent | Good |
| Z-6032 (For Comparison) | Excellent | Poor | Excellent | Fair |
| Reaction Product of 1 mole (III) with 3.0 moles of IEM | Excellent | Excellent | Excellent | Good |

γ-MPS = gamma-methacryloxypropyltrimethoxysilane
Z-6032 = Dow Corning ® Z-6032, Vinyl benzyl cationic silane
(III) = $H_2NCH_2CH_{2H}NCH_2CH_{2H}N(CH_2)_3Si(OCH_3)_3$
IEM = 2-isocyanatoethyl methacrylate

I claim:

1. A process for bonding a polymerizable material to a mineral filler comprising: (a) mixing an organosilane with a polymerizable material having aliphatic unsaturation and a filler having hydroxyl functionality thereon, to obtain a uniform dispersion of the components; and (b) polymerizing said material to form a solid composite, wherein said organosilane is represented by the formula

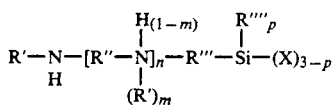

wherein R' is the group

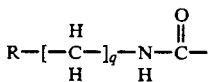

and wherein R is selected from the group consisting of acryloxy and methacryloxy radical; R" is a divalent hydrocarbon radical having 2 to 4 carbon atoms; R''' is a divalent hydrocarbon radical having 3 to 6 carbon atoms; R"" is selected from the group consisting of methyl, ethyl, propyl, butyl and phenyl; X is a hydrolyzable species selected from the group consisting of methoxy, ethoxy, acetoxy and chlorine; n is 0, 1 or 2; q is 2, 3 or 4; p is 0 or 1; and m has an average value from 0 to 1.0 when n is at least 1.

2. The process of claim 1, wherein said mixing step further comprises first treating said filler with said organosilane and then dispersing the resulting treated filler in said polymerizable material.

3. The process of claim 1, wherein R is methacrylate and q is two.

4. The process of claim 3, wherein p is zero, R" is ethylene and R''' is trimethylene.

5. The process of claim 4, wherein X is selected from the group consisting of methoxy and ethoxy radicals.

6. The process of claim 5, wherein n is 1 and X is the methoxy radical.

7. The process of claim 5, wherein said polymerizable material is selected from the group consisting of unsaturated polyesters, bis-maleimides, poly(1,2 butadiene) and acetylenic terminated polyimides.

8. The process of claim 7, wherein said polymerizable material is an unsaturated polyester.

9. The process of claim 8, wherein said filler is selected from the group consisting of silica, glass fiber, wollastonite and novacite.

10. The process of claim 2, wherein R is the methacrylate radical, q is 2, R" is ethylene, R''' is trimethylene, p is zero, and X is selected from the group consisting of methoxy and ethoxy.

11. A method for priming a surface having hydroxyl functionality thereon to improve its bonding to organic resins containing aliphatic unsaturation in the uncured state, comprising wetting said surface with a solution of an organo-silane and then drying said surface, wherein said organosilane is represented by the formula

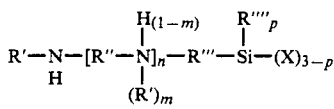

wherein R' is the group

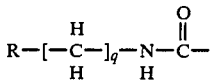

and wherein R is selected from the group consisting of acryloxy and methacryloxy radical; R" is a divalent hydrocarbon radical having 2 to 4 carbon atoms; R''' is a divalent hydrocarbon radical having 3 to 6 carbon atoms; R"" is selected from the group consisting of methyl, ethyl, propyl, butyl and phenyl; X is a hydrolyzable species selected from the group consisting of methoxy, ethoxy, acetoxy and chlorine; n is 0, 1 or 2; q is 2, 3 or 4; p is 0 or 1; and m has an average value from 0 to 1.0 when n is at least 1.

12. The method of claim 11, wherein R is methacrylate and q is two.

13. The method of claim 12, wherein p is zero, R" is ethylene and R''' is trimethylene.

14. The method of claim 13, wherein X is selected from the group consisting of methoxy and ethoxy radicals.

15. The method of claim 14, wherein said surface is selected from the group consisting of glass, metals having an oxide surface, ceramics and vitreous enamels.

16. An article of manufacture, comprising, in a dispersed and chemically reacted combination, a mineral filler; a polymerized resin, which prior to polymerization contained/ aliphatic unsaturation; and the organosilane of claim 1.

17. The article of claim 16, wherein R is methacrylate q is two, p is zero, R" is ethylene and R''' is trimethylene.

18. The article of claim 17, wherein said resin, prior to polymerization, is selected from the group consisting of unsaturated polyesters, bis-maleimides, poly(1,2 butadiene) and acetylenic terminated polyimides.

19. The article of claim 18, wherein said filler is selected from the group consisting of silica, glass fiber, wollastonite and novacite.

* * * * *